US006552214B1

(12) United States Patent
Mondello et al.

(10) Patent No.: US 6,552,214 B1
(45) Date of Patent: Apr. 22, 2003

(54) ANTIMICROBIAL COMPOUND

(75) Inventors: Frank John Mondello, Niskayuna, NY (US); Ralph Joseph May, Schenectady, NY (US)

(73) Assignee: General Electric Company, Niskayuna, NY (US)

( * ) Notice: Subject to any disclaimer, the term of this patent is extended or adjusted under 35 U.S.C. 154(b) by 0 days.

(21) Appl. No.: 09/564,232

(22) Filed: May 4, 2000

(51) Int. Cl.$^7$ ................................................ C07F 7/08
(52) U.S. Cl. ..................... 556/447; 558/424; 564/442; 568/425; 568/631; 523/122
(58) Field of Search .................... 556/447; 558/424; 564/442; 568/425, 631; 523/122

(56) References Cited

U.S. PATENT DOCUMENTS

| | | | |
|---|---|---|---|
| 3,491,137 A | * | 1/1970 | Zaweski et al. ............ 556/447 |
| 3,576,843 A | | 4/1971 | Model et al. |
| 3,642,872 A | * | 2/1972 | Model et al. ........... 556/447 X |
| 3,790,615 A | | 2/1974 | Traber et al. |
| 3,800,048 A | | 3/1974 | Model et al. |
| 4,111,844 A | | 9/1978 | Polony et al. |
| 4,501,688 A | * | 2/1985 | Braus ........................ 556/446 |
| 4,744,812 A | * | 5/1988 | Parg et al. .................. 556/446 |
| 4,935,232 A | | 6/1990 | McIntosh |
| 5,153,291 A | * | 10/1992 | Leitz et al. ................. 556/446 |
| 5,777,010 A | | 7/1998 | Nohr et al. |
| 5,853,883 A | | 12/1998 | Nohr et al. |
| 5,948,385 A | | 9/1999 | Chapman et al. |

FOREIGN PATENT DOCUMENTS

| | | |
|---|---|---|
| CH | 477164 | 10/1969 |
| CH | 508578 | 7/1971 |
| DE | 2004302 | 8/1970 |
| DE | 2832435 | 2/1979 |

OTHER PUBLICATIONS

Carte, Brad et al., "Polybrominated diphenyl ethers from *Dysidea Herbacea, Dysidea chlorea, and Phyllospongia foliascens*", Tetrahedron, vol. 37, No. 13, 1981, pp. 2335–2339.

Sharma, G.M. et al., "Antimicrobial substances of sponges. VI. Structures of two antibacterial substances isolated from the marine sponge *Dysidea Herbacea*", Tetrahedron Lett., No. 17, 1972, pp. 1715–1718.

Chemical Abstracts Service, Columbus, Ohio, US; Humppi, Tarmo: "Synthesis of polychlorinated phenoxyphenols (PCPP), phenoxyanisoles (PCPA), dibenzo–p–dioxins (PCDD), dibenzofurans (PCDF) and diphenyl ethers (PCDE)", retrieved from STN Database accession No. 106:213860.

Chemical Abstracts Service, Columbus, Ohio, US; Francesconi, K.A. et al.: "Synthesis of some polybrominated diphenyl ethers found in marine sponges", retrieved from STN Database accession No. 105:24101.

Chemical Abstracts Service, Columbus, Ohio, US; Knuutinen, Juha et al.: "Synthesis, gas chromatographic separation and structure determination of chlorinated 2–phenoxyphenols", retrieved from STN Database accession No. 99:121897.

Chemical Abstracts Service, Columbus, Ohio, US; Nilson, Carl Axel et al.: "The Synthesis of halogenated diphenyliodonium salts and their coupling products with halogenated phenols", retrieved from STN Database accession No. 88:22273.

Chemical Abstracts Service, Columbus, Ohio, US; Nilson, Carl Axel et al.: "Synthesis of chorinated 2–phenoxyphenols)", retrieved from STN Database accession No. 87:134232.

Chemical Abstracts Service, Columbus, Ohio, US; Campbell, Jo Anne B. et al.: "Electron capture nagative ion and positive ion chemical ionization mass spectrometry of olychlorinated phenoxyanisoles", retrieved from STN Database accession No. 103:5792.

Chemical Abstracts Service, Columbus, Ohio, US; Holmstedt, BO: "Mass fragmentography of TCDD and related compounds)", retrieved from STN Database accession No. 89:141675.

Chemical Abstracts Service, Columbus, Ohio, US; Nilsson, Carl Axel et al.: "Chromatographic properties of chlorinated 2–phenoxyphenols", retrieved from STN Database accession No. 87:77958.

Chemical Abstracts Service, Columbus, OH, U.S; Humppi, T. et al: "Gas chromatographic–mass spectrometric analysis chlorinated phenoxyphenols in the technical chlorophenol formulation Ky–5", retrieved from STN Database accession No. 101:40050.

* cited by examiner

Primary Examiner—Paul F. Shaver
(74) Attorney, Agent, or Firm—Andrew J. Caruso; Noreen C. Johnson

(57) ABSTRACT

A compound comprises a blocked halogenated hydroxydiphenyl ether of the formula:

(I)

$$X_4 \underset{X_5}{\overset{X_3}{\underset{\|}{\bigcirc}}} A \underset{\|}{\overset{}{\bigcirc}} O \underset{(X_2)_n}{\overset{RO}{\underset{\|}{\bigcirc}}} B \underset{}{\overset{}{\bigcirc}} X_1$$

where $X_1$ is a halogen, $X_2$ is chlorine or bromine, $X_3$ is hydrogen, chlorine or bromine, $X_4$ is chlorine, bromine, alkyl having 1 to 3 carbon atoms, —CHO, —CN or —NH$_2$, $X_5$ is chlorine, bromine, methyl, trichloromethyl, —CHO, —CN or —NH$_2$, n is 1 or 2, and R is an ether linkage inhibiting group.

28 Claims, No Drawings

ANTIMICROBIAL COMPOUND

BACKGROUND OF THE INVENTION

1. Field of the Invention

The present invention relates to an antimicrobial compound having improved resistance to conversion to a toxic compound or a dioxin-related compound.

2. Discussion of Related Art

Model et al., U.S. Pat. No. 3,800,048 and Model et al., U.S. Pat. No. 3,904,696 disclose halogenated hydroxydiphenyl ethers for controlling microorganisms. Of these, IRGASAN® DP 300 2,4,4'-dichloro-2'-hydroxydiphenyl ether produced by Ciba-Geigy Corporation, Ardsley, N.Y., is a well-known bacteriostat for industrial use. However at a temperature above about 200° C., IRGASAN® DP 300 ether converts to a chlorinated dioxin, 2,8-dichlorodibenxo-p-dioxin (DCDD), which is structurally similar to compositions suspected of causing a variety of adverse health effects including cancer.

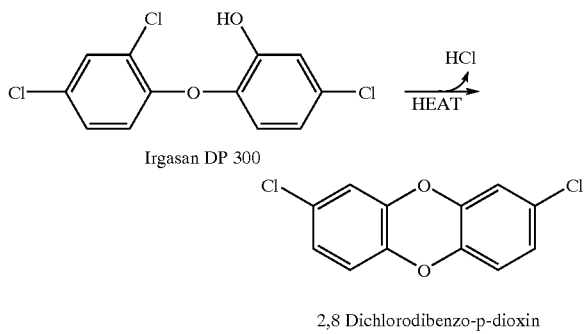

Hence, in certain applications, it may be preferable to avoid use of IRGASAN® ether such as in plastic fabrications, which may involve high temperature. As such, there is a long-felt yet unsolved need for an antimicrobial compound that can be used in higher temperature fabrications without converting to a dioxin related compound.

SUMMARY OF THE INVENTION

Accordingly, a halogenated hydroxydiphenyl ether can be reacted with a compound that imparts a functional blocking moiety to prevent the conversion of the halogenated hydroxydiphenyl ether to dioxin related compounds at the higher temperatures typically used in plastic fabrication. In one embodiment, the compound comprises a blocked halogenated hydroxydiphenyl ether of the formula:

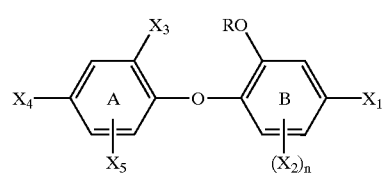

where $X_1$ is a halogen, $X_2$ is chlorine or bromine, $X_3$ is hydrogen, chlorine or bromine, $X_4$ is chlorine, bromine, alkyl having 1 to 3 carbon atoms, —CHO, —CN or —NH$_2$, $X_5$ is chlorine, bromine, methyl, trichloromethyl, —CHO, —CN or —NH$_2$, n is 1 or 2, and R is an ether linkage inhibiting group.

The invention also relates to a process for the preparation of a blocked halogenated hydroxydiphenyl ether comprising reacting a halogenated hydroxydiphenyl ether of the formula (II):

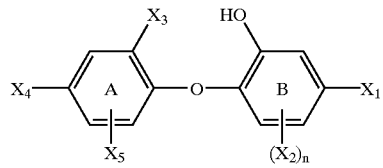

with a blocking functionality providing compound.

In another embodiment, the invention relates to an antimicrobial composition comprising a plastic and a blocked halogenated hydroxydiphenyl ether of the formula (I) and to a process for the preparation of a plastic comprising incorporating an effective amount of an antimicrobial blocked halogenated hydroxydiphenyl ether of the formula (I) into the plastic.

DETAILED DESCRIPTION OF PREFERRED EMBODIMENTS

In a preferred embodiment, an antimicrobial compound comprises a blocked halogenated hydroxydiphenyl ether of the formula:

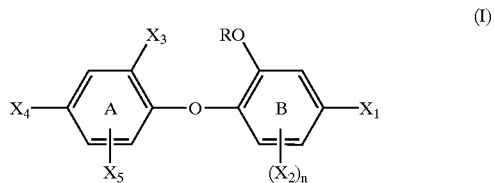

wherein $X_1$ is a halogen, $X_2$ is chlorine or bromine, $X_3$ is hydrogen, chlorine or bromine, $X_4$ is chlorine, bromine, alkyl having 1 to 3 carbon atoms, —CHO, —CN or —NH$_2$, $X_5$ is chlorine, bromine, methyl, trichloromethyl, —CHO, —CN or —NH$_2$, n is 1 or 2, and R is an ether linkage inhibiting group such as trimethylsilyl, butyldimethylsilyl, tert-butyldimethylsilyl, trifluoroacetyl, pentafluoropropionyl and heptafluorobutyryl. Other examples of R include methoxy, methyl, amino and nitro groups that inhibit the formation of an ether linkage in reaction with $X_3$.

A preferred compound of formula (I) is 2,4,4'-trichloro-2'-trimethylsilyloxy diphenyl ether according to the following formula (III):

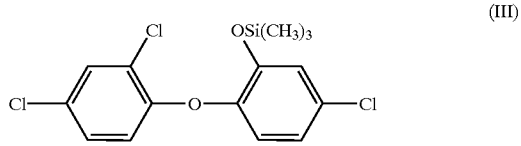

2,4,4'-trichloro-2'-trimethylsilyloxy diphenyl ether

The compounds of formula (I) can be produced by reacting a halogenated hydroxydiphenyl ether of the formula:

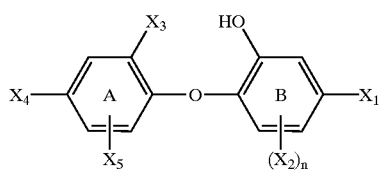

(II)

with a blocking functionality providing compound. In formula (II), $X_1$ can be a halogen, $X_2$ is chlorine or bromine, $X_3$ is hydrogen, chlorine or bromine, $X_4$ is chlorine, bromine, alkyl having 1 to 3 carbon atoms, —CHO, —CN or —NH$_2$, $X_5$ is chlorine, bromine, methyl, trichloromethyl, —CHO, —CN or —NH$_2$, and n is 1 or 2.

The blocking functionality providing compound can be any compound that will react with the hydroxyl (—OH) of formula (II) to provide a functionality that will not react with $X_3$ to result in an ether linkage between the 2,2' positions. The reaction that provides the blocking functionality can be any suitable reaction, such as silylation, acylation, or alkylation.

Suitable blocking groups include silyl groups such as trimethylsilyl, butyldimethylsilyl and tert-butyldimethylsilyl. Preferred reagents for conducting the silylation reaction include bis(trimethylsilyl) trifluoroacetamide (BSTFA), N- or O-bis (trimethylsilyl) acetamide (BSA), hexamethyldisilazane (HDMS), N-methyl-N-trimethylsilyltrifluoroacetamide (MSTFA), N-methyl-N-(tert-butyldimethylsilyl)-trifluoroacetamide (MTBSTFA) and N-trimethylsilylimidazole.

The silyl reaction can be carried out in an organic solvent such as hexane, benzene, ether or the like in the absence of water. The reaction can be conducted at a suitable temperature, for example at a temperature between about 15° and about 55° C., preferably at room temperature. Generally, the reaction is completed within about 5 minutes to about 2 hours. Desirably, the reaction is completed within about 20 minutes and preferably within about 5 minutes. The concentration of silylation reagent to starting material can be in excess of 1.0:1.0 on a per mole basis, preferably in excess of 3.0:1.0.

Additionally, an acylation reaction can be used to provide a blocking functionality. The acylation can convert the 2' hydroxyl group of the halogenated hydroxydiphenyl ether into an ester through the action of a carboxylic acid or carboxylic acid derivative. Preferred acylating agents include perfluoroacylimidazoles such as trifluoroacetylimidazole (TFAI), pentafluoropropionylimidazone (PFPI) and heptafluorobutyrylimidazole (HFBI).

The acylation reaction can be conducted in an organic solvent such as hexane or benzene at a temperature, for example, between about 15° and about 55° C., preferably at room temperature. Typically, the reaction is completed within 5 minutes but the reaction time can be extended to 1 hour. Concentration of acylation reagent to starting material can be in excess of 1.0:1.0 on a per mole basis, preferably in excess of 3.0:1.0.

Another suitable blocking providing reaction is alkylation wherein the hydrogen of the 2' hydroxyl group of the halogenated hydroxydiphenyl ether is replaced with an aliphatic or aliphatic-aromatic group. Pentafluorobenzylbromide (PFBBr) is an example of a suitable alkylating compound.

The alkylation reaction can be carried out in a suitable organic solvent such as methylene chloride with tetrabutylammonium as a counter ion. The reaction can be conducted at a temperature for example between about 15° and about 55° C., preferably at room temperature. Typically, the reaction is completed within 5 minutes but the reaction time can be extended to 24 hours. Concentration of alkylating reagent to starting material can be in excess of 1.0:1.0 on a per mole basis, preferably in excess of 3.0:1.0.

The diphenyl ethers can be used in combination with other antimicrobially active substances. For example, the compound can be used with halogenated salicylic acid alkyl amides and anilides, with halogenated diphenyl ureas, with halogenated benzoxazoles or benzoxazolones, with polychlorohydroxydiphenyl methanes, with halogendihydroxydiphenyl sulfides, with bactericidal 2-imino-imidazolidines or tetrahydropyrimidines or with biocidal quaternary compounds or with certain dithiocarbamic acid derivatives such as tetramethyl thiuram disulphide. Various additional antimicrobial substances alone or in combination can be used with the diphenyl ethers to broaden the range of antimicrobial action and/or to provide a synergistic effect.

The diphenyl ether according to formula (I) can be incorporated into a plastic composition by addition into a polymer prior to the formation of pellets or by the addition of the ether in powder form immediately prior to or during a melt stage of a molding process. The diphenyl ether can be provided in a powder form, as pellets or as a blend of ether-containing pellets and non-ether-containing pellets.

The antimicrobial compound can be incorporated into a wide variety of plastics such as melt-extrudable thermoplastic polymers, which can be melt-processed to form non-woven webs or other shaped articles. The term "plastic" includes both thermosetting and thermoplastic materials. Particularly useful thermoplastic materials are thermoplastic polyolefins including any thermoplastic polyolefin used for the preparation of shaped articles by melt extrusion. Examples include polyethylene, polypropylene, poly(1-butene), poly(2-butene), poly(1-pentene), poly(2-pentene), poly(3-methyl-1-pentene), poly(4-methyl-1-1pentene), 1,2-poly-1,3-butadiene, 1,4-poly-1,3-butadiene, polyisoprene, polychloroprene, polyacrylonitrile, poly(vinyl acetate), poly-(vinylidene chloride), polystyrene and the like. Also included are blends of two or more polyolefins and copolymers.

The antimicrobial composition can be used with other suitable commercial plastic materials such as polyamide resins, acrylonitrile-butadiene-styrene (ABS) thermoplastic resins, polycarbonate resins, polycarbonate-ABS blends, PBT resins, acrylic-styrene-acrylonitrile (ASA), polyetherimides, interpolymers of PPO and expandable polystyrene EPS, polyphenylene ether+polystyrene (PPE-PPS blends), polyphenylene sulfide (PPS) based polymers, polybutylene terephthalate (PBT) based polymers, alloy blends of (PBT) and polycarbonate (PC), polypropylene, and polyethylene.

In this embodiment, the antimicrobial composition contains an effective amount of the antimicrobial compound. In this context, the term "effective amount" is that amount which exhibits desirable antimicrobial activity at a point of use. In various alternative embodiments, the antimicrobial composition can contain between about 0.001 and about 5%, preferably between about 0.005 and about 3% and more preferably between about 0.01 and about 1% by weight of the antimicrobial compound.

The following example is provided in order that those skilled in the art will be better able to understand and practice the present invention. This example is intended to serve as an illustration and not as a limitation of the present invention as defined in the claims herein.

EXAMPLE

Dioxin formation was compared between modified and unmodified IRGASAN® bacteriostat samples. It was determined that 2,8 DCDD was produced during analysis of unmodified IRGASAN® bacteriostat by gas-chromatography-mass spectroscopy (GC-MS), presumably during injection of the material at 270° C. (518° F.). Injection of a 1000 ppm solution of IRGASAN® resulted in the production of approximately 46 ppm of DCDD.

The structure of IRGASAN® bacteriostat was modified by derivatization with BSTFA. A 0.1 ml volume of BSTFA (Supelco inc.) was added to 1.0 ml of a 1000 ppm IRGASAN® solution. Dioxin levels were undetectable upon analysis of the modified IRGASAN® solution by GC-MS.

Antimicrobial activity of the modified IRGASAN® bacteriostat was compared to that of the unmodified material in a Kirby-Bauer type assay. Three solutions of IRGASAN® bacteriostat and three solutions of modified IRGASAN® bacteriostat (3, 30 and 3000 ppm) were prepared and soaked into Whatman filter paper disks ~6 mm in diameter and allowed to dry. The disks were placed onto the surface of nutrient agar plates that had been inoculated with $1 \times 10^6$ cells of either *E. coli* or *Pseudomonas aeruginosa*. The ability of the compounds to inhibit bacterial growth was determined by measuring the diameter of the zone of inhibition surrounding the filter paper disks after 24 h of incubation. The results (TABLE 1) indicate that there is no difference in activity between the modified and unmodified IRGASAN® bacteriostat compound.

TABLE 1

| Concentration (ppm) | Zone of Inhibition (mm) | |
|---|---|---|
| | *E. coli* | *P. aeruginosa* |
| 0 ppm | 0 | 0 |
| 3 ppm Unmodified | 1 | 0 |
| 3 ppm modified | 1 | 0 |
| 30 ppm Unmodified | 4 | 0 |
| 30 ppm Modified | 4 | 0 |
| 3000 ppm Unmodified | 12 | 0 |
| 3000 ppm Modified | 12 | 0 |

It will be understood that each of the elements described above, or two or more together, may also find utility in applications differing from the types described herein. While the invention has been illustrated and described as embodied in an antimicrobial compound, it is not intended to be limited to the details shown, since various modifications and substitutions can be made without departing in any way from the spirit of the present invention. For example, additional antimicrobial substances or microbe abatement methodology can be used in concert with the present compound or process when needed. Although many examples of various alternative chemicals, materials, and reaction components have been presented throughout this specification, the omission of a possible item is not intended to specifically exclude its use in or in connection with the claimed invention. As such, further modifications and equivalents of the invention herein disclosed may occur to persons skilled in the art using no more than routine experimentation, and all such modifications and equivalents are believed to be within the spirit and scope of the invention as defined by the following claims.

What is claimed is:

1. A compound comprising a blocked halogenated hydroxydiphenyl ether of the formula:

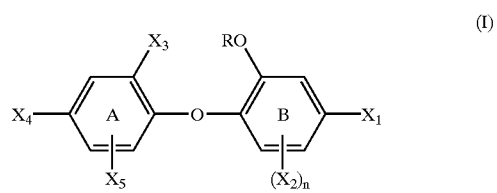

where $X_1$ is a halogen, $X_2$ is chlorine or bromine, $X_3$ is hydrogen, chlorine or bromine, $X_4$ is chlorine, bromine, alkyl having 1 to 3 carbon atoms, —CHO, —CN or —NH$_2$, $X_5$ is chlorine, bromine, methyl, trichloromethyl, —CHO, —CN or —NH$_2$, n is 1 or 2, and R is trimethylsilyl, butyldimethylsilyl, or tert-butyldimethylsilyl.

2. A compound comprising a blocked halogenated hydroxydiphenyl ether of the formula:

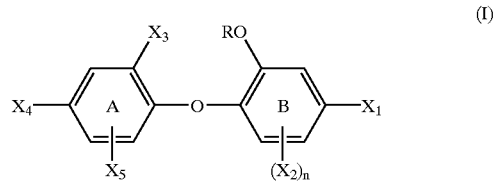

where $X_1$ is a halogen, $X_2$ is chlorine or bromine, $X_3$ is hydrogen, chlorine or bromine, $X_4$ is chlorine, bromine, alkyl having 1 to 3 carbon atoms, —CHO, —CN or —NH$_2$, $X_5$ is chlorine, bromine, methyl, trichloromethyl, —CHO, —CN or —NH$_2$, n is 1 or 2, and R is pentafluorobenzyl.

3. The compound of claim 1, comprising 2,4,4'-trichloro-2'-trimethylsilyloxy diphenyl ether.

4. A process for the preparation of a blocked halogenated hydroxydiphenyl ether, comprising reacting a halogenated hydroxydiphenyl ether with a blocking functionality providing compound, said halogenated hydroxydiphenyl ether having the formula:

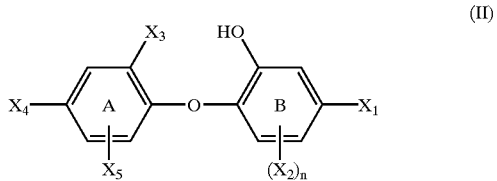

where $X_1$ is a halogen, $X_2$ is chlorine or bromine, $X_3$ is hydrogen, chlorine or bromine, $X_4$ is chlorine, bromine, alkyl having 1 to 3 carbon atoms, —CHO, —CN or —NH$_2$ and $X_5$ is chlorine, bromine, methyl, trichloromethyl, —CHO, —CN or —NH$_2$ and n is 1 or 2.

5. The process of claim 4, wherein said blocking functionality providing compound reacts with the —OH of compound (II) to provide an ether linkage inhibiting group.

6. The process of claim 4, wherein said blocking functionality providing compound reacts with the —OH of compound (II) to provide a blocked halogenated hydroxydiphenyl ether of the formula:

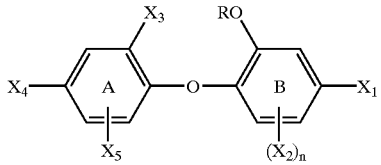

(I)

where $X_1$ is a halogen, $X_2$ is chlorine or bromine, $X_3$ is hydrogen, chlorine or bromine, $X_4$ is chlorine, bromine, alkyl having 1 to 3 carbon atoms, —CHO, —CN or —NH$_2$, $X_5$ is chlorine, bromine, methyl, trichloromethyl, —CHO, —CN or —NH$_2$, n is 1 or 2, and R is an ether linkage inhibiting group.

7. The process of claim 4, wherein said blocking functionality providing compound provides a silyl group.

8. The process of claim 7, wherein said blocking functionality providing compound provides a trimethylsilyl, butyl-dimethylsilyl or tert-butyldimethylsilyl group.

9. The process of claim 4, wherein said blocking functionality providing compound is bis(trimethylsilyl), trifluoroacetamide (BSTFA), N-bis (trimethylsilyl) acetamide, O-bis (trimethylsilyl) acetamide (BSA), hexamethyldisilazane (HDMS), N-methyl-N-trimethylsilyltrifluoroacetamide (MSTFA), N-methyl-N-(tert-butyldimethylsilyl)-trifluoroacetamide (MTBSTFA), or N-trimethylsilylimidazole.

10. The process of claim 4, wherein said blocking functionality providing compound is a perfluoroacylimidazole.

11. The process of claim 10, wherein said blocking functionality providing compound is trifluoroacetylimidazole (TFAI), pentafluoropropionylimidazone (PFPI), or heptafluorobutyrylimidazole (HFBI).

12. The process of claim 4, wherein said blocking functionality providing compound is pentafluorobenzylbromide (PFBBr).

13. An antimicrobial composition, comprising a plastic and a blocked halogenated hydroxydiphenyl ether of the formula:

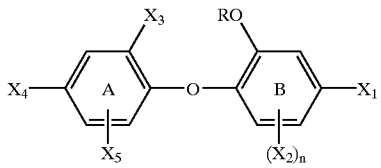

(I)

where $X_1$ is a halogen, $X_2$ is chlorine or bromine, $X_3$ is hydrogen, chlorine or bromine, $X_4$ is chlorine, bromine, alkyl having 1 to 3 carbon atoms, —CHO, —CN or —NH$_2$, $X_5$ is chlorine, bromine, methyl, trichloromethyl, —CHO, —CN or —NH$_2$, n is 1 or 2, and R is an ether linkage inhibiting group.

14. The antimicrobial composition of claim 13, comprising between about 0.001 and about 5% by weight of the antimicrobial compound.

15. The antimicrobial composition of claim 13, comprising between 0.005 and about 3% by weight of the antimicrobial compound.

16. The antimicrobial composition of claim 13, comprising between 0.01 and about 1% by weight of the antimicrobial compound.

17. The antimicrobial composition of claim 13, wherein the plastic is a melt-extrudable thermoplastic polymer.

18. The antimicrobial composition of claim 13, wherein the plastic is a thermosetting polymer or thermoplastic polymer.

19. The antimicrobial composition of claim 13, wherein the plastic is a polyolefin.

20. The antimicrobial composition of claim 13, wherein the plastic is polyethylene, polypropylene, poly(1-butene), poly(2-butene), poly(1-pentene), poly(2-pentene), poly(3-methyl-1-pentene), poly(4-methyl-1-1pentene), 1,2-poly-1,3-butadiene, 1,4-poly-1,3-butadiene, polyisoprene, polychloroprene, polyacrylonitrile, poly(vinyl acetate), poly-(vinylidene chloride) or polystyrene.

21. The antimicrobial composition of claim 13, wherein the plastic is a blend of polyolefins or copolymers.

22. The antimicrobial composition of claim 13, wherein the plastic is a polycarbonate.

23. The antimicrobial composition of claim 13 in the form of a pellet or powder.

24. The antimicrobial composition of claim 13, wherein R is trimethylsilyl, butyldimethylsilyl, or tert-butyldimethylsilyl.

25. The antimicrobial composition of claim 13, wherein R is an acyl group that inhibits the formation of an ether linkage with $X_3$.

26. The antimicrobial composition of claim 13, wherein R is pentafluorobenzyl.

27. The antimicrobial composition of claim 13, wherein said blocked halogenated hydroxydiphenyl ether 2,4,4'-tricloro-2'-trimethylsilyloxy diphenyl ether.

28. A process for the preparation of an antimicrobial plastic, comprising incorporating into said plastic, an effective amount of a blocked halogenated hydroxydiphenyl ether of the formula:

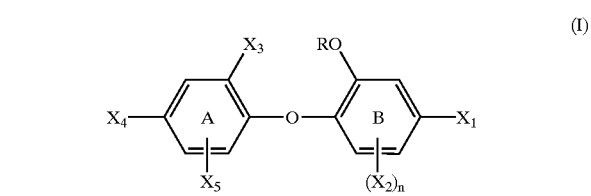

(I)

where $X_1$ is a halogen, $X_2$ is chlorine or bromine, $X_3$ is hydrogen, chlorine or bromine, $X_4$ is chlorine, bromine, alkyl having 1 to 3 carbon atoms, —CHO, —CN or —NH$_2$, $X_5$ is chlorine, bromine, methyl, trichloromethyl, —CHO, —CN or —NH$_2$, n is 1 or 2, and R is an ether linkage inhibiting group.

* * * * *